US008314628B2

(12) United States Patent
Clarysse et al.

(10) Patent No.: US 8,314,628 B2
(45) Date of Patent: Nov. 20, 2012

(54) METHOD AND DEVICE FOR THE INDEPENDENT EXTRACTION OF CARRIER CONCENTRATION LEVEL AND ELECTRICAL JUNCTION DEPTH IN A SEMICONDUCTOR SUBSTRATE

(75) Inventors: Trudo Clarysse, Antwerp (BE); Fabian Dortu, Leuven (BE)

(73) Assignee: IMEC, Leuven (BE)

( * ) Notice: Subject to any disclaimer, the term of this patent is extended or adjusted under 35 U.S.C. 154(b) by 1468 days.

(21) Appl. No.: 11/763,401

(22) Filed: Jun. 14, 2007

(65) Prior Publication Data

US 2007/0292976 A1 Dec. 20, 2007

Related U.S. Application Data

(63) Continuation of application No. PCT/EP2005/013423, filed on Dec. 12, 2005.

(30) Foreign Application Priority Data

Dec. 14, 2004 (GB) .................................. 0427318

(51) Int. Cl.
*G01R 31/308* (2006.01)
(52) U.S. Cl. ............. 324/754.23; 356/237.1; 356/237.2; 250/307
(58) Field of Classification Search ............. 324/754.23; 356/237.1, 237.2; 250/307
See application file for complete search history.

(56) References Cited

U.S. PATENT DOCUMENTS

| 5,042,952 | A | 8/1991 | Opsal et al. |
| 6,049,220 | A | 4/2000 | Borden et al. |
| 6,323,951 | B1 * | 11/2001 | Borden et al. ................ 356/502 |
| 6,392,756 | B1 * | 5/2002 | Li et al. ......................... 356/632 |
| 7,307,735 | B2 * | 12/2007 | Hecht et al. ................... 356/504 |

FOREIGN PATENT DOCUMENTS

| EP | 0 827 192 A2 | 3/1998 |
| EP | 0 827 192 A3 | 2/1999 |
| WO | WO 2005/017996 | 2/2005 |

OTHER PUBLICATIONS

P. Borden, et al., "Carrier Illumination Characterization of Ultra-Shadow Implants", Handbook of Silicon Semiconductor Metrology, edited by A.C. Diebold, (Dekker Inc., New York, 2001), 97.
T. Clarysse, et al., "Accurate electrical activation characterization of CMOS ultra-shallow profiles", Materials Science and Engineering B, Elsevier Sequoia, Lausanne, CH, pp. 166-173, Presented on May 27, 2005 during E-MRS Spring Meeting 2004 in Strasbourg.
Lena Nicolaides et al., "Nondestructive analysis of ultrashallow junctions using thermal wave technology", Jan. 2003, Review of Scientific Instruments, American Institute of Physics, US, pp. 586-588.
International Search Report dated May 22, 2006, issued in International Application No. PCT/EP2005/013423.

* cited by examiner

*Primary Examiner* — Arleen M Vazquez
(74) *Attorney, Agent, or Firm* — Knobbe Martens Olson & Bear LLP

(57) ABSTRACT

The present invention provides a method and device for determining, in a non-destructive way, carrier concentration level and junction depth in a semiconductor substrate, independent from each other, during a single measurement.

24 Claims, 15 Drawing Sheets

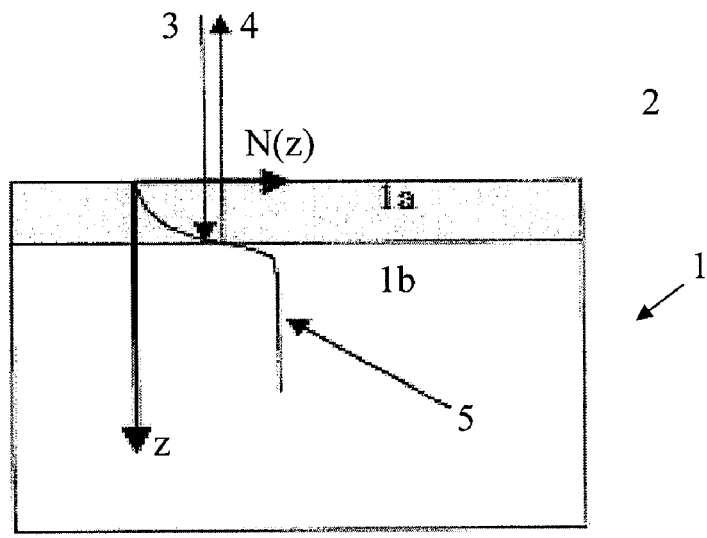
Fig. 1 – PRIOR ART
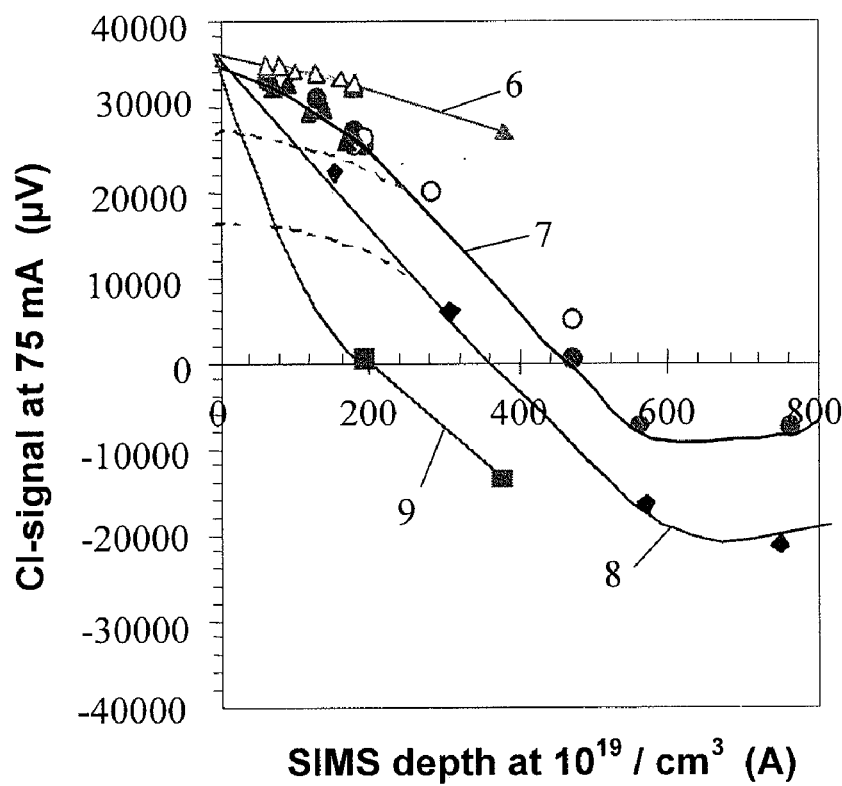
Fig. 2 - PRIOR ART

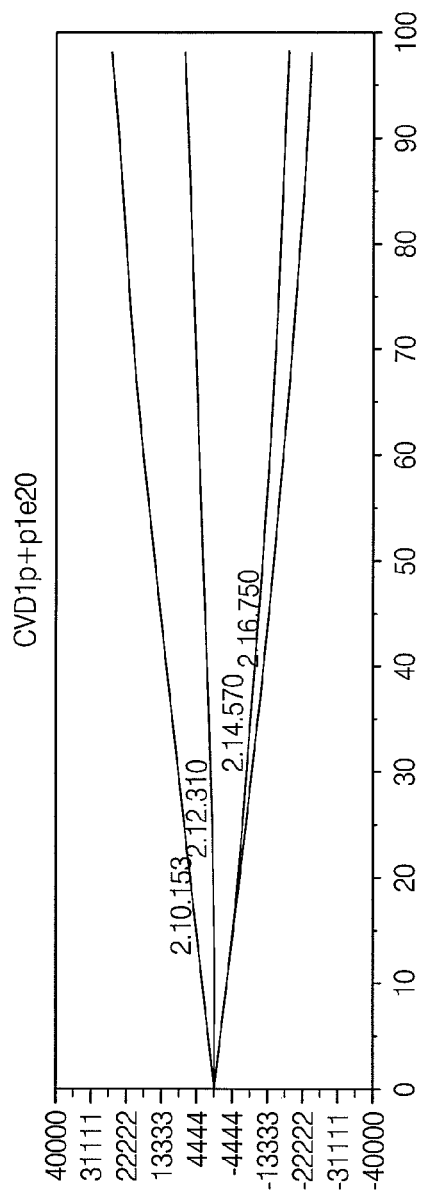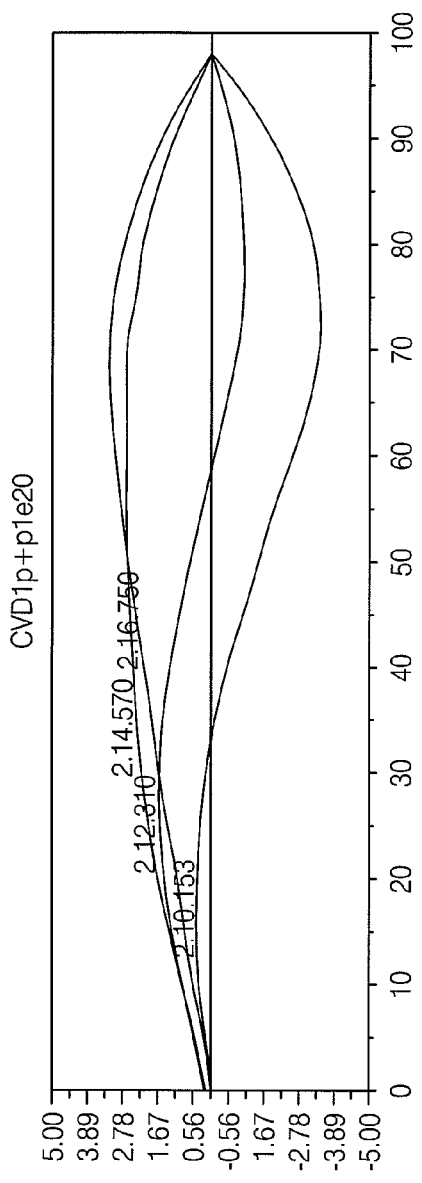
FIG. 9B

METHOD AND DEVICE FOR THE INDEPENDENT EXTRACTION OF CARRIER CONCENTRATION LEVEL AND ELECTRICAL JUNCTION DEPTH IN A SEMICONDUCTOR SUBSTRATE

CROSS REFERENCE TO RELATED APPLICATIONS

This application is a continuation of International Application PCT/EP2005/013423, filed on Dec. 12, 2005. The entire disclosure of this application is incorporated by reference in its entirety.

BACKGROUND OF THE INVENTION

1. Field of the Invention

Certain inventive aspects relate to non-destructive optical measurement techniques for determining the dopant carrier profile in semiconductor layers, using optical energy to create charge carriers in these semiconductor layers and to probe changes in reflectivity created by these charge carriers. More particularly, certain inventive aspects relate to a method for the independent extraction of the peak dopant concentration and junction depth in a particular semiconductor substrate, from a single measurement as well as devices and software for carrying out the methods.

2. Description of the Related Technology

In semiconductor processing, methods are required for the determination of properties of semiconductor materials, such as Si, SiGe, GaAs, . . . , and their dependence on processing conditions. Introducing species into a semiconductor material by, for example, ion implantation can change the properties of the bulk material. Other methods that can change the properties of the bulk material are manufacturing of the substrate, annealing such as for example rapid thermal processing (RTP) or rapid thermal annealing (RTA), etc.

In CMOS (Complementary Metal Oxide Silicon) devices for example, it is important to be able to determine the junction depth and profile of the source and drain regions formed in the semiconductor substrate. For advanced high-performance Complementary Metal-Oxide-Semiconductor (CMOS) technologies, it is, for example, crucial to be able to quickly and reliably characterize ultra shallow junctions. As CMOS structures, such as for example transistors, become increasingly smaller (<50 nm), dopant profiles shrink accordingly (unction depths less than 20 nm) and their exact determination becomes more difficult and at the same time more critical. Process conditions can be optimized to obtain the desired junction depth and profile and, hence, to obtain the required device characteristics.

Various methods exist to investigate the properties of the semiconductor dopant profile. Some of these techniques, however, are destructive. One example of such destructive techniques is spreading-resistance-profile (SRP), whereby a semiconductor substrate to be characterized is cleaved along a diagonal cleavage line and a two point electrical measurement is then performed at subsequent positions along this cleavage line. Other known techniques are non-destructive techniques such as, for example, the Carrier Illumination™ (CI) technique, as disclosed in U.S. Pat. No. 6,049,220 and U.S. Pat. No. 6,323,951, both hereby incorporated by reference in their entirety. For example for in-line monitoring of the pre- and post-anneal process steps, this Carrier Illumination™ technique has established itself as a fast, non-contact, non-destructive tool having wafer mapping capability. For process monitoring applications, the exact quantitative interpretation of the CI-signal is less important as long as high repeatability and sensitivity for a particular profile or process parameter can be demonstrated.

The CI technique uses optical reflectance to measure junction depth. It is based on the linear decrease ($\beta<0$) of the index of refraction of a semiconductor with the carrier concentration, as expressed by equation (1):

$$n = n_0 + \beta N \quad (1)$$

wherein:
n is the index of refraction of the doped semiconductor material,
$n_o$ is the index of refraction of the semiconductor material in absence of a carrier concentration (being for example 3.42 for silicon),
N is the free carrier concentration, and
$\beta$ is a constant.

In practice, the concentration-dependent term is in the range of $5.10^{-3}$ or less, too low thus to contrast the doped layer against the substrate. The CI technique takes advantage of excess carrier pile-up at the edge of the doped layer to obtain sufficient contrast. By illuminating the doped region, excess carriers are created. In the quasi-static regime in which CI operates, the excess carriers move through diffusion and drift. The concentration of excess carriers, which is determined by the difference in carrier concentration with and without illumination, rises steeply at the edge of the doped region.

In CI and similar techniques such as, for example, the Thermo-Probe technique, typically, two lasers are used. A first laser is a focused pump laser or generation laser, generating a "pump" laser beam or generation beam. The first laser operates at a fixed wavelength, which is larger than the band gap of the semiconductor material under study and typically is about 830 nm. This laser is used to generate a quasi-static excess carrier profile in the bulk of the semiconductor material, giving rise to a depth dependent index of refraction of the material. The excess carriers distribute themselves in the semiconductor material according to a profile which is defined as the carrier concentration and is expressed in number of carriers per $cm^3$ exceeding the level of carriers present within the semiconductor substrate without stimulation, this latter being labelled as the background carrier concentration or profile, e.g. in the absence of illumination. This background carrier concentration is dependent on the concentration of dopant atoms. Specifically, the excess carrier concentration changes from zero outside a surface of the semiconductor material to a finite value inside the semiconductor material. This change in excess carrier concentration results in a steep increase in the concentration of excess carriers at the surface of the semiconductor substrate. This steep increase of the excess carriers concentration at the interface between the semiconductor material under study and its surroundings, e.g. air, will be labelled as the near-surface component which will result in a near-surface component of a reflected probe beam as will be discussed later on. As the depth z, which is defined from the front surface of the semiconductor substrate into the semiconductor substrate, increases, the excess carrier concentration changes proportionally to the change in the concentration of dopant atoms or to the presence of recombination centers. For example, in some cases, the dopant concentration rises, but in other cases the dopant concentration dips first and then rises, depending on the detailed shape of the doping profile.

In the CI technique, a CI-signal to be measured is then generated by illuminating the optically stimulated semiconductor material with a second "probe" laser, generating a probe laser beam or probe beam, which may also be labelled analyzer beam, having a fixed wavelength which is higher than the fixed wavelength of the "pump" laser and typically is about 980 nm. This probe laser beam will be reflected at the sample surface and/or at any region with a large change in the index of refraction proportional to the excess carrier profile, as is illustrated in FIG. 1 (see below). Reflected light from the second laser provides a profile depth signal. Use of photon energy at or below the band gap of the material under study minimizes excess carrier generation by the second laser, so that the power of the first laser exclusively determines the excess carrier profile for sufficiently high power settings.

Reflected signals are converted to a value representative of junction depth using an algorithm developed through extensive correlation of CI-measurements with SRP measurements on a wide range of implants. The primary parameter reported is the profile depth at a pre-selected concentration, for example, $1 \times 10^{18}/cm^3$. Algorithms are available for n/p, p/n and p/p structures.

FIG. 1 shows a semiconductor substrate 1 and a probe laser beam 3 impinging from the surroundings 2 on the semiconductor substrate 1. The incident probe laser beam 3 and reflected probe laser signal 4 are indicated by respectively arrows 3 and 4. The semiconductor substrate 1 comprises a doped layer 1a formed on an undoped or lower doped region 1b. The substrate 1 can be formed by depositing an in-situ doped layer 1a on top of layer 1b, yielding a uniform doping profile over region 1a or can be formed by implanting dopants into the substrate 1, yielding a doped region 1a and an undoped region 1b.

By using e.g. ion implantation for implanting dopants into the substrate 1, any kind of doping profile can be obtained depending on the choice of implant species, the energy and implantation dose used. Layer 1a can be doped with a dopant of the same or the opposite type of dopant used to dope the underlying layer 1b. In FIG. 1, the excess carrier profile N(z) as function of depth z into the substrate 1 is also shown, indicated by graph 5. The probe laser beam (arrow 3) will be reflected, thus generating the reflected probe laser signal (arrow 4) at various positions on the semiconductor substrate 1. For example, the probe laser beam 3 may be reflected at the surface, yielding a surface component in the reflected probe laser signal 4. It may also be reflected by a change in the excess carrier profile which can occur at the surface, yielding a near-surface component, or at the interface between the doped part 1a and undoped part 1b on the gradient of N(z), yielding a bulk component. The original purpose of the measurement is to extract from the total reflected signal 4 the reflected probe signal originating from the bulk of the device, as only the remaining signal will give information about the doping profile. Therefore, ideally the surface and the near-surface components should be eliminated from the total reflected signal 4.

Laser beams from both lasers, pump laser and probe laser, are superimposed onto each other and may contact the semiconductor substrate 1 in the same or in a different area. Typically, both lasers are in a fixed measurement set-up and both incident laser beams have a direction perpendicular to the wafer surface or substrate surface, meaning incident at a zero angle relative to the wafer surface normal. An important difference between the excess carriers and the background carriers—which also create an index gradient—is that the excess carrier concentration can be modulated. A slow modulation of the pump laser, typically at 1 kHz, is used to allow the reflection of the probe laser signal by the excess carriers to be detected using phase-locked methods while maintaining quasi-static conditions. The modulation and the diffusion of the generated excess carrier in the semiconductor substrate 1 are in phase with the modulation of the pump laser.

The reflected probe power is given by the following theoretical formula, which is given by P. Borden, et al in "Carrier Illumination Characterization of Ultra-Shallow Implants", in Handbook of Silicon Semiconductor Metrology, edited by A. C. Diebold, (Dekker Inc., New-York, 2001), 97, hereby incorporated by reference in its entirety:

$$E_r^* E_r = r_s^2 E_0^2 \left\{ \underbrace{1 - \frac{\beta_n t^2}{r_s}}_{A} \left( \underbrace{N_{surf}}_{B} + \underbrace{\int_{0+}^{\infty} \cos(2kn_{Si}z) \frac{dN(z)}{dz} dz}_{C} \right) - \underbrace{\frac{\beta_p t^2}{r_s}}_{} \left( \underbrace{P_{surf}}_{D} + \underbrace{\int_{0+}^{\infty} \cos(2kn_{Si}z) \frac{dP(z)}{dz} dz}_{E} \right) \right\} \quad (2)$$

wherein $$\beta_n = -\frac{q^2}{2m_n \omega^2 \varepsilon_0 \sqrt{\varepsilon}} \quad (2a)$$

and $$\beta_p = -\frac{q^2}{2m_p \omega^2 \varepsilon_0 \sqrt{\varepsilon}} \quad (2b)$$

and wherein
  $E_0$ and $E_r$ are respectively the incident and reflected probe signal electromagnetic field,
  $r_s$ is the reflection coefficient at the air-substrate interface (in particular for a Silicon interface $r_s=-0.549$),
  $\beta_n$ and $\beta_p$ are negative electron- and hole-related constants which involve, among others factors, electron and hole effective masses,
  t is the transmission coefficient at the air-substrate interface,
  $N_{surf}$ and $P_{surf}$ are the surface electron and hole excess carrier levels,
  $k=2\pi/\lambda$ is the field propagation constant in vacuum,
  $n_{Si}$ is the substrate material index of refraction (in particular the silicon index of refraction $n_{si}=3.435$ at 980 nm),
  z is the depth defined from the front surface into the semiconductor substrate,
  N(z) and P(z) are respectively the electron and hole excess carrier profiles,
  q is the elementary electron charge,
  $m_n$ and $m_p$ are the electron and hole optical effective masses,
  $\omega$ is the angular frequency ($\omega=k.c$, where c is the speed of light),
  $\varepsilon_0$ and $\varepsilon$ are the dielectric constants of vacuum and the semiconductor substrate material, e.g. silicon, respectively.

In equation (2), 0+ refers to the semiconductor side of the air-semiconductor interface, meaning that the integral is taken from immediately beneath the semiconductor surface into the bulk of the semiconductor substrate.

Equation (2) can be written as:

$$\text{power}=\text{constant}(A-[B+C]-[D-E]) \quad (3)$$

Whereby:
  The A-component represents the reflection of the probe laser beam at the air-semiconductor interface. This is a constant term that is independent of the modulation of the pump laser.
  The B-component represents the reflection of the probe laser beam near the surface by dopant related excess electrons. This component is modulated by the modulation of the pump laser. The integral ranges from 0 to 0+, indicating that the large value of the derivative dN(z)/dz at the air-semiconductor interface is being accounted for.

The C-component represents the reflection of the probe laser beam in the bulk, meaning the reflection by excess electrons in the region of the active dopant profile away from the surface. This component is modulated by the modulation of the pump laser. The integral ranges from 0+, which is just underneath the surface, into the bulk of the semiconductor material, indicating that the large value of the derivative dN(z)/dz at the air-semiconductor interface is not accounted for and only changes of this derivative of the excess electron profile in the bulk are taken into account.

The D-component represents the reflection of the probe laser beam near the surface by dopant related excess holes. This component is modulated by the modulation of the pump laser. The integral ranges from 0 to 0+, indicating that the large value of the derivative dP(z)/dz at the air-semiconductor interface is accounted for.

The E-component represents the reflection in the bulk, meaning the reflection by excess holes in the region of the active dopant profile away from the surface. This component is modulated by the modulation of the pump laser. The integral ranges from 0+ into the bulk of the semiconductor material indicating that the large value of the derivative dP(z)/dz at the air-semiconductor interface is not accounted for and only changes of this derivative of the excess hole profile in the bulk are taken into account.

Since the first term (A) in equation (2), i.e. the surface reflection in the absence of any carriers, is a pure dc component, only the second (B+C) and third (D+E) modulation related terms in equation (2), which follow the pump laser modulation, represent the actual CI-signal.

The first part (B, D) of the second term (B+C) and third term (D+E) in equation (2), involving $N_{surf}$ and $P_{surf}$, are termed the (modulation-related) near-surface components. It has been found by the inventors that these near-surface components (B, D) can significantly contribute to the total signal if the peak concentration level of the dopant profile drops below $10^{20}$/cm$^3$. This is due to the longer Auger lifetimes for lower doping levels. Consequently, a high CI-signal is measured on lowly doped bulk substrates. The presence of the near-surface component complicates the extraction of the dopant interface (junction) depth position from CI-signal versus depth response curves and/or signal versus pump laser power curves for unknown structures, because of the significant dependence of the position of these response/power curves on the near-surface component contribution.

The above-described problem is illustrated in FIG. 2. FIG. 2 illustrates correlation curves of the CI-signal, taken at a predetermined pump laser power, which in the example given may be 75 mA, versus SIMS junction depth at a predetermined concentration, in the example given 1e19/cm$^3$, for CVD grown layers (box-profile) with different peak carrier levels. A graph such as in FIG. 2 can be created by performing the following subsequent steps:

creating a dopant profile in the semiconductor substrate 1 with a known peak/surface concentration for one type of species, measuring the CI-signal of this dopant profile for a predetermined pump signal power, for example, a pump signal power of 75 mA, measuring the junction depth at a selected concentration level using SIMS, plotting both points (SIMS depth at selected concentration level, CI-signal at selected power) on FIG. 2, repeating the above sequence measuring samples having a dopant profile for this species with the same peak concentration but various depths to create a correlation curve, repeating the above sequence for different types of dopants or concentration levels to create additional correlation curves.

In FIG. 2, curve 6 is valid for CVD grown layers with a dopant concentration of 1e19 cm$^{-3}$, curve 7 for CVD grown layers with a dopant concentration of 5e19 cm$^{-3}$, curve 8 for CVD grown layers with a dopant concentration of 1e20 cm$^{-3}$ and curve 9 for CVD grown layers with a dopant concentration of 3e20 cm$^{-3}$. It has to be noted that these CVD grown layers were only active for about 50% of their nominal peak dopant value, based on Four Point Probe measurements. This means that, for example, a dopant concentration of 5e19 cm$^{-3}$ would result in an active dopant concentration of 2.5e19 cm$^{-3}$. When measuring the CI-signal for an unknown doping profile in the CVD grown layers, it is impossible to extract the corresponding junction depth from FIG. 2, as long as one does not know the exact peak carrier concentration level, i.e. one does not know which correlation curve to take.

SUMMARY OF CERTAIN INVENTIVE ASPECTS

It is an object of certain inventive aspects to provide a method and device for independently extracting the peak dopant concentration and junction depth in a semiconductor substrate from a single measurement. The method may be, amongst others, suitable for determining the dopant carrier profile in semiconductor layers having highly-lowly doped structures, i.e. structures having a dopant or carrier concentration profile which shows a maximum near the surface and is decreasing towards the bulk of the substrate, such as for example semiconductor layers formed and/or doped by CVD, implantation, or diffusion. Such highly-lowly doped structures may be considered as structures having a dopant profile that has a maximum near the surface and decreases towards the substrate (Gaussian, box-like).

In a first aspect of the invention, an optical measurement method is provided for determining a dopant concentration profile, characterized by a concentration level and a junction depth, of a semiconductor substrate. The optical measurement method is for use with:

first correlations between first amplitudes of measured reflection signals obtained by creating different concentrations of excess carriers and a probe laser beam at least partially reflected by the excess carriers, on first substrates of a semiconductor material having a dopant profile, characterized by a concentration level and a junction depth, and dopant concentration levels for a dopant in the first substrates, and a second correlation between the first amplitudes of the measured reflected signals and junction depths of the dopant profile of the first substrates.

The method comprises:

measuring a second amplitude of a reflection signal obtained by creating excess carriers and impinging a probe laser beam at least partially reflected by the excess carriers, on the semiconductor substrates having a dopant profile, characterized by a concentration level and a junction depth, and determining from the first and second correlations and the second amplitude the junction depth and the corresponding dopant concentration level for the semiconductor substrate.

Creating excess carriers may comprise impinging a pump laser beam.

The semiconductor substrate may, for example, comprise silicon, germanium, galliumarsenide, or any other suitable semiconductor material.

The method allows to independently extract the peak dopant concentration and junction depth in a particular semiconductor substrate, from a single measurement. The method furthermore may be applied to any non-destructive method, such as for example carrier illumination and thermal wave techniques.

In an embodiment of the present invention, measuring the first or the second amplitude comprises:
    measuring the reflection signal as a function of the pump power level, thus yielding a power curve, the power curve showing an inflection point,
    determining a first pump power level value corresponding to the inflection point, and
    determining the reflection signal at a second pump power level.

Determining a junction depth and a carrier concentration level for the substrate may comprise determining a carrier concentration level from the reflection signal at the second pump power level and the first pump power level corresponding to the inflection point.

Determining the reflection signal may, in some embodiments, be carried out at a first predetermined value of the pump laser power, e.g. 75 mA pump laser power, and determining the carrier concentration level from the reflected signal may be carried out at a second predetermined value of the pump laser power, the first pump laser power corresponding to the inflection point. The first and the second value of the pump laser power can be the same.

According to a particular embodiment of the present invention, the method may comprise:
    generating excess carriers in a semiconductor substrate
    impinging on the semiconductor substrate a probe laser beam, the probe laser beam being at least partially reflected by the excess carriers, on a semiconductor substrate,
    measuring the reflected signal as a function of pump laser power, thus yielding a power curve, the power curve showing an inflection point,
    determining a first pump laser power value corresponding to the inflection point,
    determining the reflected signal at a second pump laser power, and
    determining a carrier concentration level from the reflected signal at the second pump laser power and the pump laser power corresponding to the inflection point.

The substrate may be a highly-lowly doped structure. With a highly-lowly doped structure is meant a structure having a dopant profile with a maximum near the surface and decreasing towards the bulk of the substrate. Examples of highly-lowly doped structures are structures formed and/or doped by CVD (chemical vapor deposition), implantation, diffusion, etc. In one particular embodiment of the invention, the substrate may have a box-like dopant profile.

In further embodiments, the optical measurement method may furthermore comprise determining a junction depth of the semiconductor substrate from the reflection signal at a second pump laser power and the determined carrier concentration level.

In embodiments of the invention, generating a reflection signal may comprise:
    generating an excess charge carrier profile in the semiconductor substrate by focusing a pump laser beam onto the semiconductor substrate, and
    illuminating the semiconductor substrate with a probe laser beam.

According to embodiments of the invention, the inflection point is determined based on a constant value of the second derivative of the power curve, this constant value of the second derivative of the power curve possibly equaling zero.

In embodiments of the invention, the optical measurement method may be based on the carrier illumination technique. In that case, the pump laser beam may have a fixed wavelength of e.g. about 830 nm and may have a photon energy which is larger than the energy band gap of the semiconductor material without doping.

In a further embodiment of the first aspect of the present invention, measuring the first or the second amplitude of the reflection signal may comprise determining a component of the reflection signal which is in phase with the pump laser signal and determining a component of the reflection signal which is in about 90° phase difference with the pump laser signal. The power level of the pump laser signal may be a pre-determined level.

Determining a junction depth and a carrier concentration level for the substrate may comprise determining a carrier concentration level from an amplitude of the reflection signal which is in phase with the pump laser signal and from an amplitude of the reflection signal which is in 90° phase difference with the pump laser signal. Determining a junction depth and a carrier concentration level for the substrate may furthermore comprise determining a junction depth from the determined component of the reflection signal which is in 90° phase difference with the pump laser signal and from the determined carrier concentration level.

The substrate may be a highly-lowly doped structure. With a highly-lowly doped structure is meant a structure having a dopant profile with a maximum near the surface and decreasing towards the bulk of the substrate. Examples of highly-lowly doped structures are structures formed and/or doped by CVD (chemical vapor deposition), implantation, diffusion, etc. In one particular embodiment of the invention, the substrate may have a box-like dopant profile.

In embodiments of the present invention, generating a reflection signal may comprise:
    generating an excess charge carrier profile in the semiconductor substrate by focusing a pump laser beam onto the semiconductor substrate, and
    illuminating the semiconductor substrate with a probe laser beam.

In embodiments of the invention, the optical measurement method may be based on the thermal wave technology. In that case, the pump laser beam may have a fixed wavelength of e.g. about 790 nm.

In a second aspect of the present invention, an optical measurement method is provided for calibration of a substrate of a semiconductor material having a dopant profile, characterized by a concentration level and a junction depth, in the substrate. The method comprises:
    determining a first set of correlation curves between
    first components of measured reflection signals obtained by creating different concentrations of excess carriers in the substrate and a probe laser beam at least partially reflected by the excess carriers, on the substrate and
    dopant concentration levels for a dopant in the substrate, and determining a second correlation between the amplitudes of the measured reflected signal and junction depths of the substrate.

Creating a first set of correlation curves may comprise:
providing at least two semiconductor substrates with predetermined different dopant profiles, each dopant profile characterized by a concentration level and junction depth,
measuring for each semiconductor substrate a first amplitude of reflected signals, the reflecting signals being generated by creating different concentrations of excess carriers in the sample, and a probe laser beam at least partially being reflected by the excess carriers, on the substrate,
determining a first correlation between the first measured amplitude of each reflected signal and the concentration level of the at least two semiconductor substrates.

Determining a second correlation may comprise determining a second correlation between the first measured amplitude of each reflected signal and the junction depth of the at least two semiconductor substrates.

A third inventive aspect provides an apparatus for performing measurement of a bulk property of a semiconductor substrate. The apparatus comprises:
an illumination device comprising a means for creating excess carriers and a probe laser for impinging a laser beam at least partially reflected by the excess carriers, on the semiconductor substrate, thus generating a reflection signal,
first storing means for storing first correlations between first amplitudes of measured reflection signals and dopant concentration levels for a dopant in the substrates,
second storing means for storing second correlations between the first amplitudes of the measured reflection signals and junction depths of the dopant profile of the substrate,
means for measuring second amplitudes of measured reflection signals, and
means for determining from the stored first and second correlations and the measured second amplitudes the junction depth and the dopant concentration level for the semiconductor substrate.

According to embodiments of the present invention, the apparatus may comprise:
a carrier illumination device comprising a pump laser and a probe laser for impinging laser beams on the semiconductor substrate, thus generating a reflection signal,
means for measuring the reflection signal as a function of pump laser power, thus yielding a power curve, the power curve showing an inflection point,
means for determining a first pump laser power value corresponding to the inflection point,
means for determining the reflected signal at a second pump laser power; and
means for determining a carrier concentration level from the reflected signal at the second pump laser power and the first pump laser power corresponding to the inflection point.

An apparatus according to one inventive aspect may furthermore comprise means for determining a junction depth of the semiconductor substrate from the reflected signal at the second pump laser power and the determined concentration level.

The pump laser may generate a pump laser beam with a fixed wavelength, of e.g. about 830 nm.

According to embodiments of the present invention, an apparatus may comprise:
an illumination device comprising a pump laser and a probe laser for impinging laser beams on the semiconductor substrate, thus generating a reflection signal,
means for measuring first components of the reflection signal, and
means for determining a carrier concentration level from the measured first components of the reflection signal.

The apparatus may furthermore comprise means for determining a junction depth of the semiconductor substrate for a measured first component of the reflection signal and the determined concentration level.

The pump laser may generate a pump laser beam with a fixed wavelength, e.g. of about 790 nm.

A further aspect provides a computer program product for executing the method according to embodiments of the present invention when executed on a computer device. Furthermore, a machine readable data storage device is provided for storing the computer program product.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 1 is an illustration of the conventional Carrier Illumination™ technique.

FIG. 2 shows correlation curves of the CI-signal, taken at a predetermined pump laser power of 75 mA, versus SIMS junction depth at a predetermined concentration of 1e19, for CVD grown layers (box-like profiles) with different peak carrier levels.

DETAILED DESCRIPTION OF CERTAIN INVENTIVE EMBODIMENTS

Figure 3:
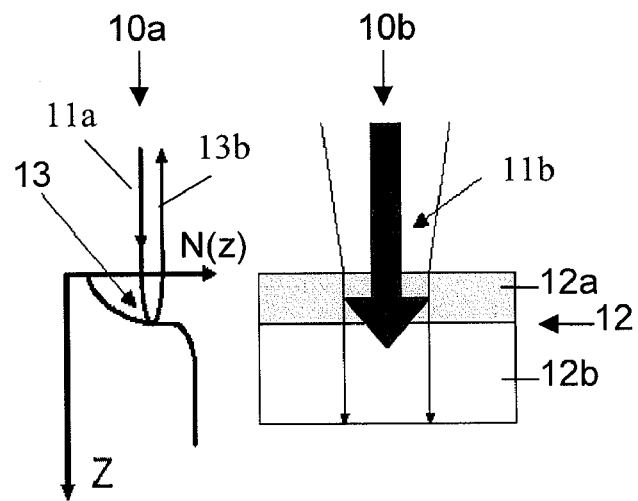
FIG. 3 illustrates the Boxer Cross Carrier Illumination™ technique according to an embodiment of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The invention will now be described by a detailed description of several embodiments of the invention. It is clear that other embodiments according to the invention can be configured according to the knowledge of persons skilled in the art without departing from the true spirit or technical teaching of the invention, the invention being limited only by the terms of the appended claims.

For the purpose of teaching the invention, the description discusses the application of the invention for the conventional Carrier Illumination™ technique, based on a closer investigation of the CI power curves. In the further description, when using the term CI power curves, a representation is meant of the variation of the CI-signal (y-axis) versus the pump laser power (x-axis). However, the invention can also be applied to any other non-destructive measurement technique using a pump laser to create excess carriers in a semiconductor substrate and at least one probe laser whose reflection in the semiconductor substrate is correlated to the presence of the excess carriers. Instead of the CI-signal, the value of a parameter representative or characteristic for the respective non-destructive technique should then be determined and plotted on the y-axis, yielding a curve representing the variation of that parameter as a function of the pump laser power.

The method according to the invention may be used for determining the carrier concentration level and electrical junction depth in a semiconductor substrate having a highly-lowly doped structure. With highly-lowly doped structure is meant a structure having a dopant profile with a maximum near the surface and decreasing towards the bulk of the substrate. Examples of highly-lowly doped structures may be structures formed and/or doped by CVD (chemical vapor deposition), implantation, diffusion, . . . .

In FIG. 3 the basic idea or methodology of Boxer Cross Carrier Illumination as applied by one embodiment is illustrated. Again, it has to be mentioned that this is only meant for explanation of the embodiment and that it is not limiting the embodiment. The embodiment may also be applied to other non-destructive techniques such as, for example, the thermal wave technique. As already described, Carrier Illumination™ uses two lasers, i.e. a probe laser $10a$ generating a probe laser beam $11a$, e.g. an infrared (IR) laser beam, and a pump laser $10b$ generating a pump laser beam $11b$, e.g. a red laser beam, both laser beams $11a$, $11b$ impinging on a semiconductor substrate 12, e.g. a silicon substrate, comprising a doped layer $12a$ and an undoped (or lower doped) layer $12b$. The incident pump laser beam, indicated by arrow $11b$, excites an excess charge carrier distribution $N(z)$ in the substrate 12. The impinging probe laser beam $11a$ reflects, as indicated by arrow 13, due to index of refraction changes which are due to gradients of the charge carrier distribution $N(z)$. For phase sensitive measurement, the carrier illumination signal depends on the strength of the reflected signal 13 and its position (depth) below the surface of the semiconductor substrate 12.

Figure 4:
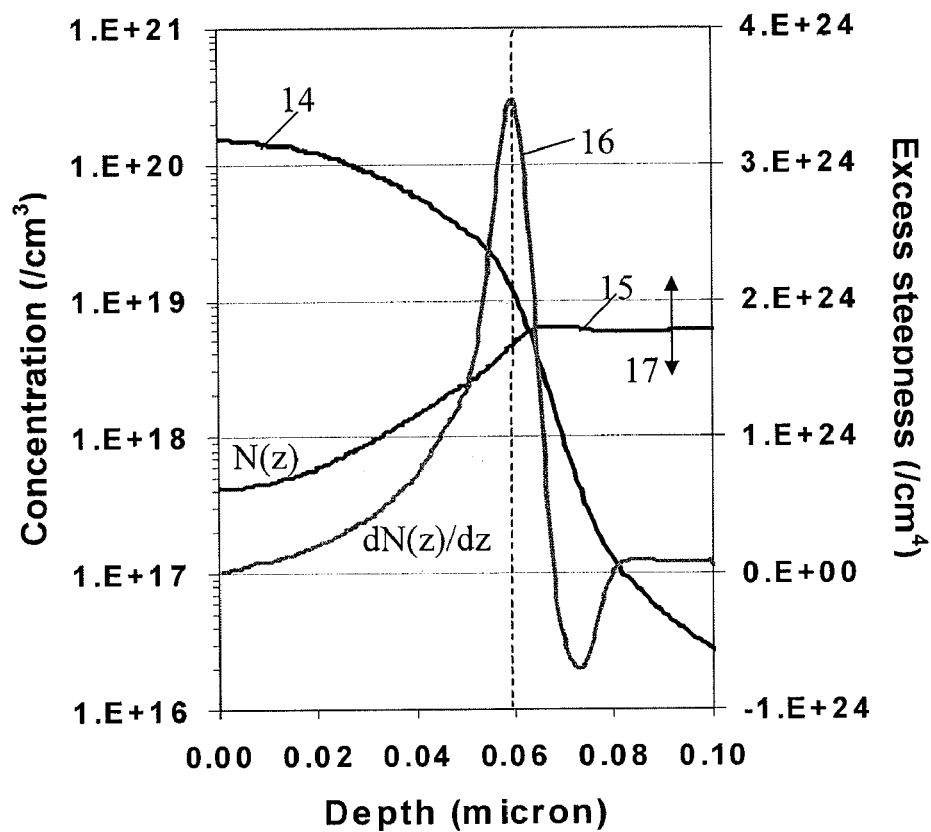
FIG. 4 shows a dopant concentration, excess carrier concentration and derivative of the excess carrier concentration versus depth into the substrate illustrating the interaction between excess carrier concentration and dopant profile.

Typically, CI-measurements involve the monitoring of the CI-signal as the generation power of the pump laser $10b$ is swept from low to full power. The resulting curves, plotting CI-related signals as a function of the pump laser power, are referred to as power curves. As the level of excess carriers will increase proportionally to the applied generation power, one might, in a simplistic view, expect a proportional increase of the CI-signal. FIG. 4 illustrates this mechanism. In this figure, the dopant concentration (curve 14), the excess carrier profile (curve 15) and the derivative of the excess carrier profile (curve 16) are plotted as a function of the dept into the semiconductor substrate 12. As the charge carrier injection level increases with increasing power of the pump signal, as indicated by arrow 17 in FIG. 4, one also probes different concentration levels along the slope of the dopant profile, and thus probes different profile depths, leading to a further change in the CI-signal. As such, the power curve will also contain information on the profile abruptness. For abrupt profiles, $dN(z)/dz$ (curve 16) peaks where the profile reaches the injection level, as illustrated by the vertical dashed line in FIG. 4.

A disadvantage of the CI technique, and for most of the optical measurement techniques which may be used to determine a dopant profile of a semiconductor layer, is that the CI-junction depth depends on the carrier profile, the kind of dopant, the dopant concentration, etc. For example, the CI-signal is strongly dependent on the peak dopant concentration. Hence, one problem that arises is that of determining the junction depth when the carrier profile is unknown.

In general, the CI-signal may arise from a combination of three components:
  a primary one, the surface component, originating from the reflection of the probe laser beam $11a$ on the air-semiconductor substrate interface;
  a second one, the near surface component, originating from the reflection on near-surface carriers, and a third one, the interface component, originating from reflection on dopant related injected excess carriers at the interface between the doped region 12a and the undoped or lower doped region 12b of the semiconductor substrate 12.

One embodiment provides a method for independently extracting the peak dopant concentration and junction depth in a semiconductor substrate or layer from a same measurement by performing a detailed analysis of the dependency of the location of the inflection point in the power curve as a function of the characteristic reflected signal, i.e., in the case of the carrier illumination technique, the CI-signal, at a predetermined reference laser power, for example, at a predetermined reference laser power of 75 mA. In the further description, the reflected signal will be referred to as CI-signal. It is, however, to be understood that this is not limiting to the invention and that, in case of other non-destructive methods used to determine peak carrier concentration levels in a semiconductor substrate, the reflected signal may be another signal than a CI-signal.

Figure 5:
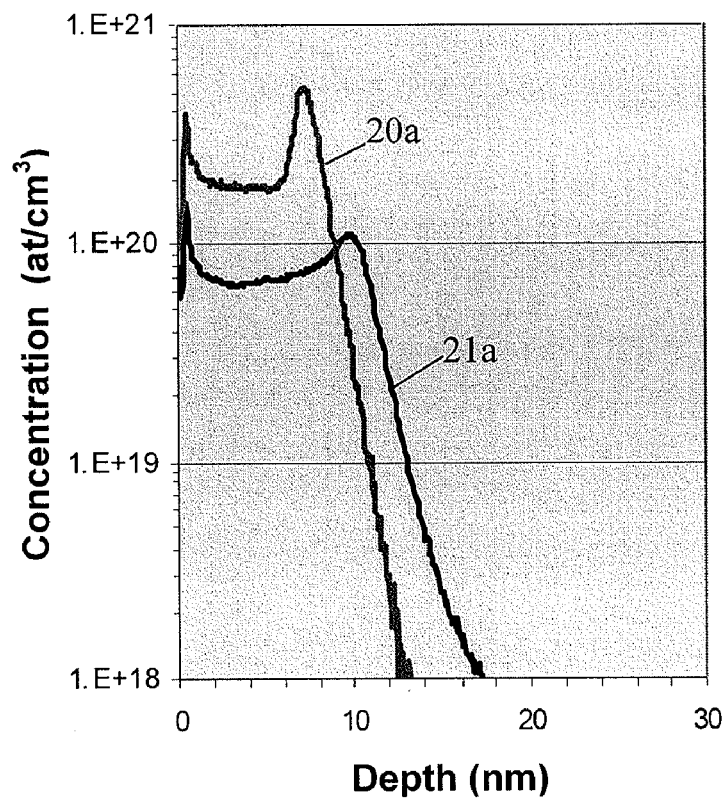
FIG. 5 shows the dopant profiles of two CVD layers with almost the same junction depth, but significantly different peak carrier concentration levels.

The basic underlying idea of one embodiment is illustrated in FIGS. 5 to 8. FIG. 5 shows the dopant profiles (curve 20a and curve 21a) of two semiconductor layers both formed by the CVD (chemical vapor deposition) technique and having almost the same junction depth, but with significantly different peak carrier concentration levels. The CVD technique is a known technique to form layers in semiconductor technology. In CVD, gaseous precursors, e.g. $SiH_4$ or $GeH_4$, are used to form semiconductor layers of resp. Si or Ge. If precursors are added which comprise dopants, for example $BCl_3$ to provide B, these Si or Ge semiconductor layers are doped during formation. As the concentration of these precursors can be varied during the deposition process, complex layer structures with varying dopant concentrations can be built up. In the example given in FIG. 5, the precursor concentration was kept constant and hence, a box-like profile was created, i.e. the semiconductor layer formed had a constant dopant concentration over its entire thickness, this concentration being higher than the undoped or lowly doped substrate on which this doped layer was formed.

Figure 6:
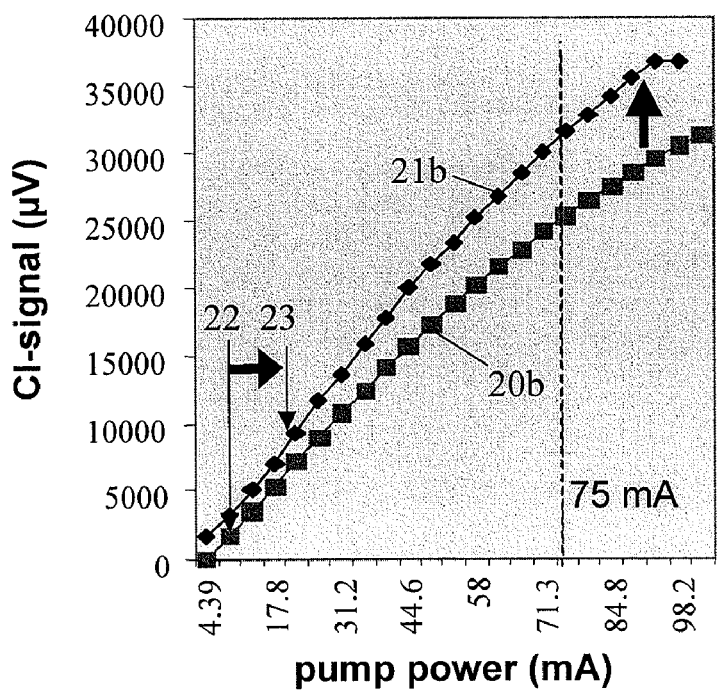
FIG. 6 shows the CI power curves corresponding to the curves of FIG. 5.
Figure 7:
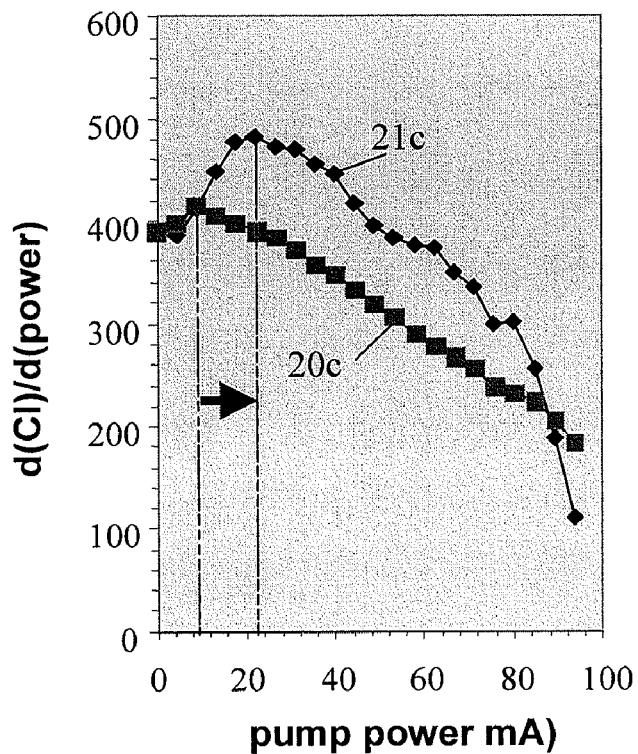
FIG. 7 shows the first derivative of the power curves of FIG. 6.
Figure 8:
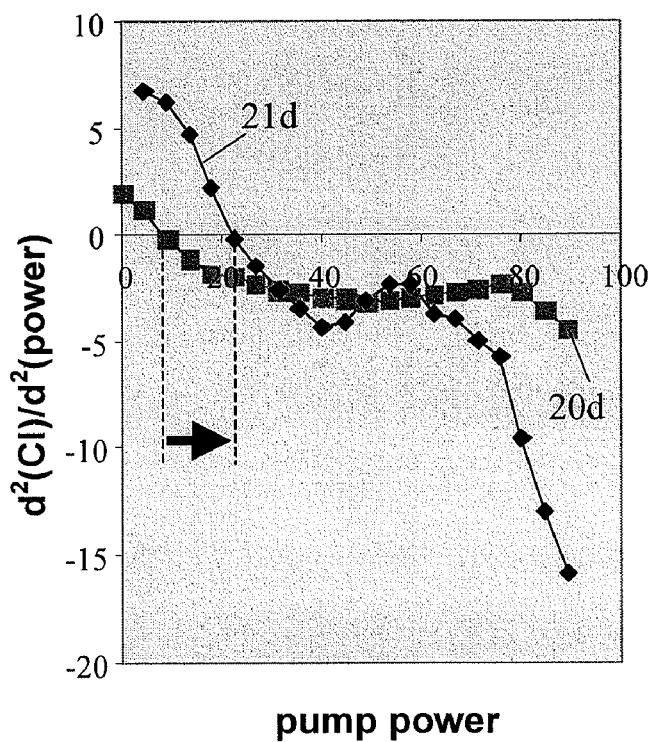
FIG. 8 shows the second derivative of the power curves of FIG. 7.

Curve 20a in FIG. 5 represents the concentration versus depth curve for a first sample CVD2-1 which has been formed by a low temperature deposition process such as CVD. Curve 21a represents the concentration versus depth curve for a second sample CVD3-DO2, formed by a similar process as the first sample. FIG. 6 shows the CI-signal versus power curves 20b and 21b corresponding to respectively curve 20a and 21a of FIG. 5. The power curve 21b for the lower doped CVD structure is the highest due to the larger contribution of the near surface term (see eq. (2)). This is, however, not the only difference between both power curves 20b and 21b. When considering the first derivatives of both curves, respectively curve 20c and 21c (see FIG. 7), one can see that the pump laser power at which they have their respective maximum value is distinctly different. This can even be better seen on the plot of the second derivative, respectively curve 20d and 21d (see FIG. 8), where it is the intersection of the curves 20d, 21d with the x-axes (zero value of second derivative) that is different. These intersection points relate to the inflection points in the original power curves 20a and 21b of FIG. 6, indicated by respectively arrow 22 and arrow 23.)

According to one embodiment, it is proposed to use the difference in pump laser power at which the inflection points occur to discriminate between the effect of the carrier concentration level and the junction depth on the reflected signal, i.e. in the examples given, the CI-signal. The method is therefore, in these examples, based on the systematic correlation of the pump power laser setting at which an inflection point occurs in the CI power curves with respect to the involved carrier concentration levels and junction depths. When other techniques than the CI technique are used, it is the inflection point in the characteristic parameter of the respective technique versus pump laser power which is used in the method.

Figure 9A:
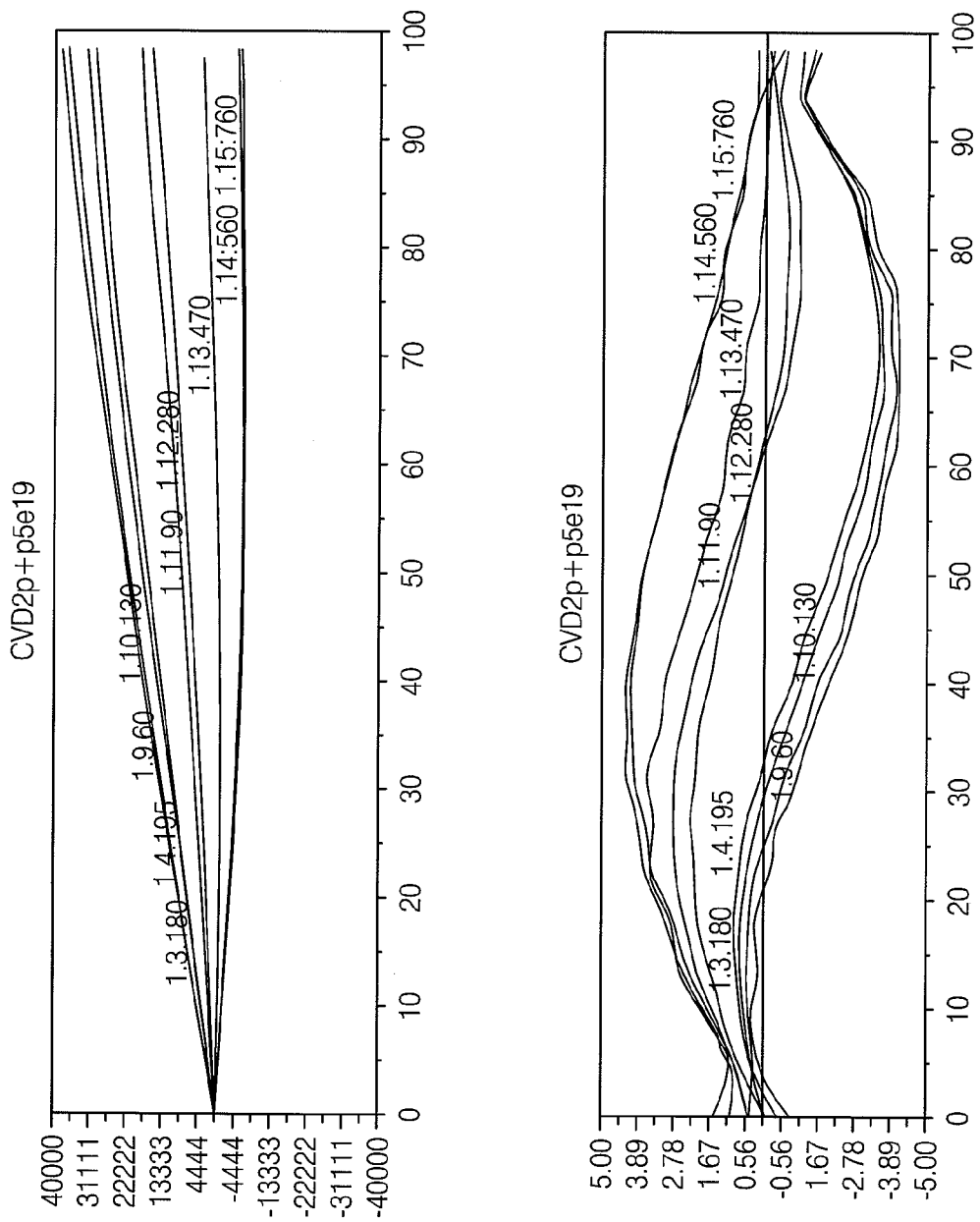
FIG. 9 shows power curves (left hand side) and their corresponding second derivatives (right hand side) for a series of CVD layers with different peak carrier levels and junction depths.
Figure 9C:
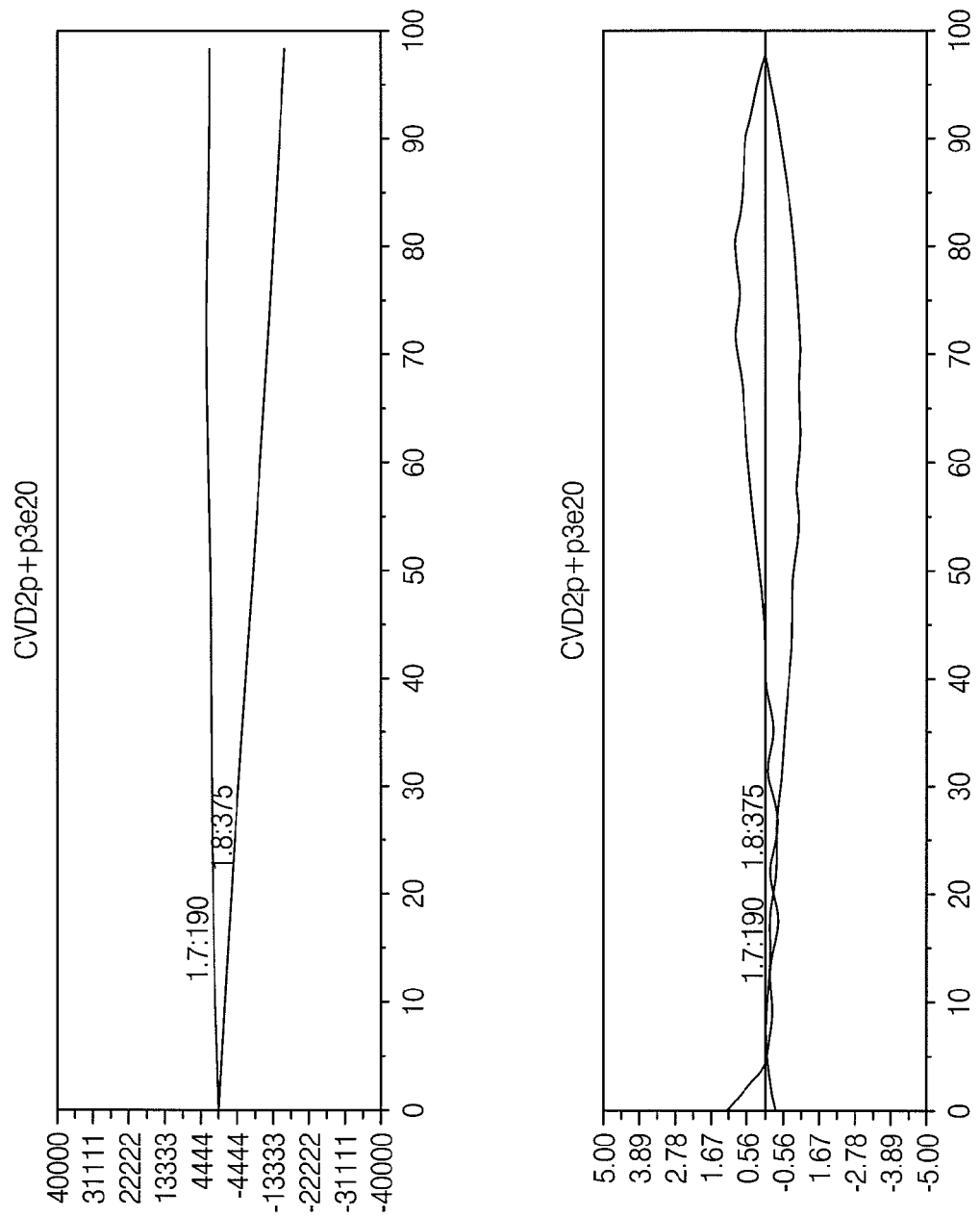
Figure 9D:
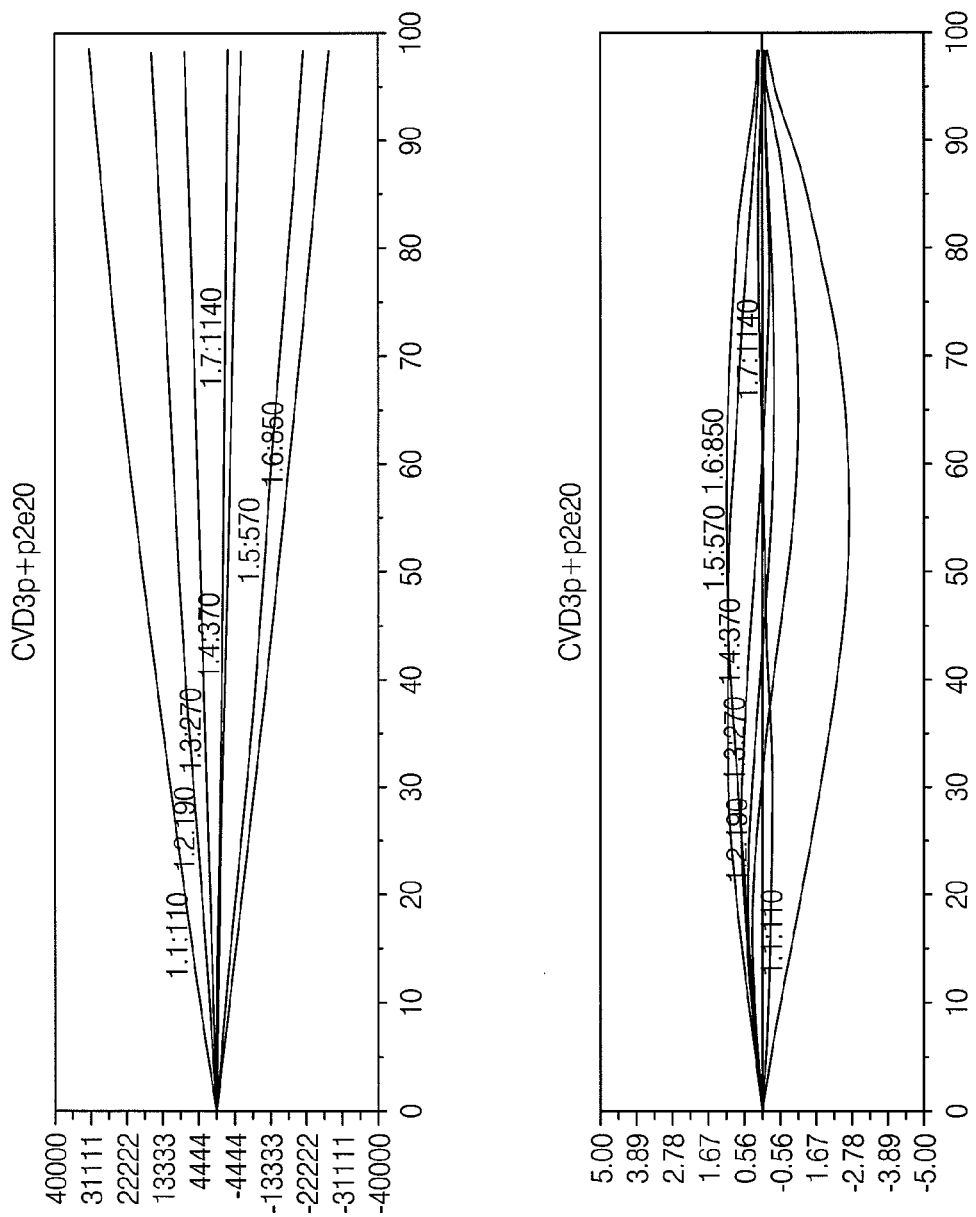

FIG. 9 shows power curves (left hand curves—CI-signal (μV) versus pump power (in % of the maximum power)) and their corresponding second derivative (right hand curves) for a series of CVD layers with different peak carrier levels and junction depths. Each graph shows the variation for a fixed peak carrier level and different junction depths. The a) curves relate to a peak active carrier level of $5e19$ $cm^{-3}$, the b) curves relate to a peak active carrier level of $1e20$ $cm^3$, the c) curves relate to a peak active carrier level of $3e20$ $cm^3$, and the d) curves relate to a peak active carrier level of $2e20$ $cm^{-3}$. The position (x-value of the pump power) of the inflection point of the power curve corresponds with the position of the zero value of the second derivative of the power curve.

Figure 10:
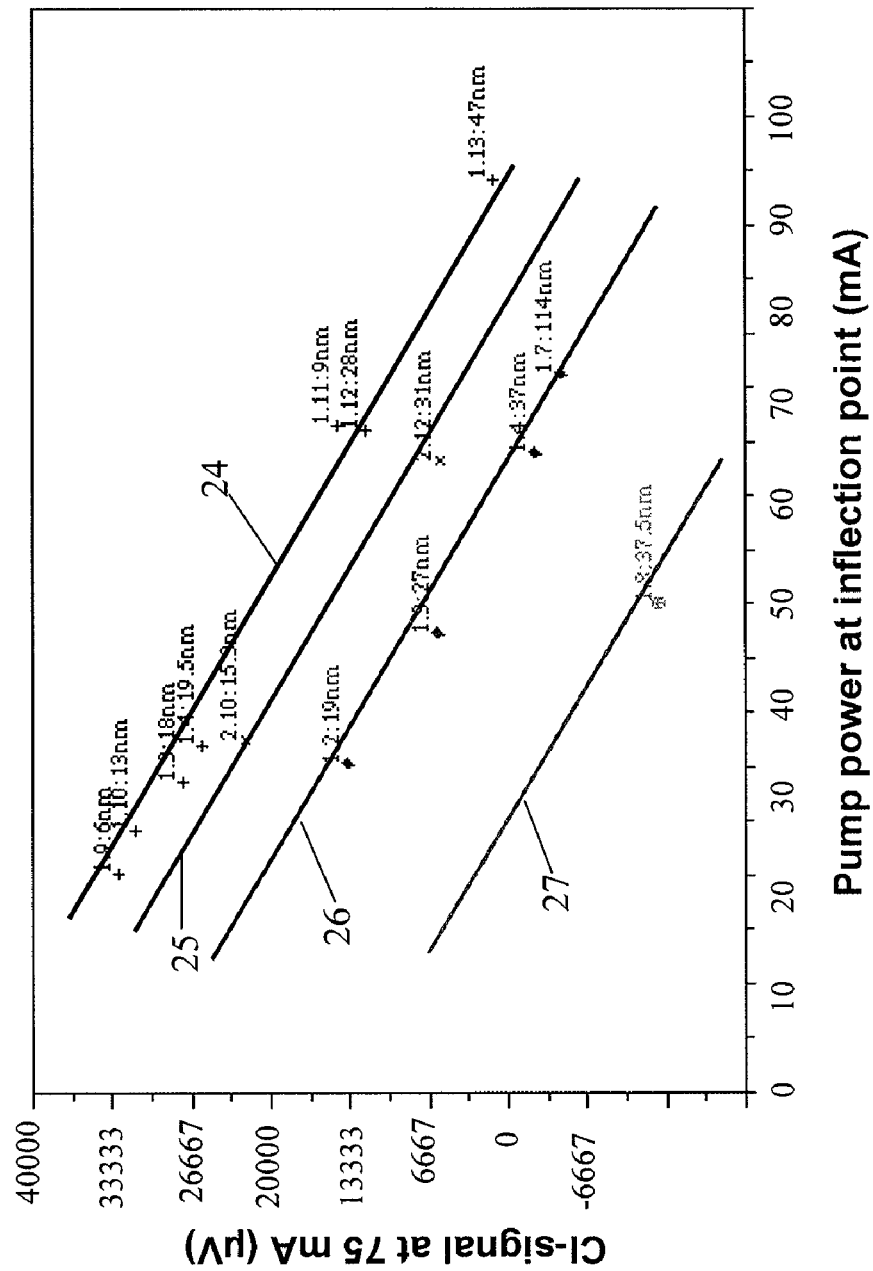
FIG. 10 shows the experimental correlation of the CI-signal at a pre-selected pump power of 75 mA versus pump laser power at the power curve inflection point for different CVD samples with different dopant concentrations according to an embodiment of the present invention.
Figure 13:
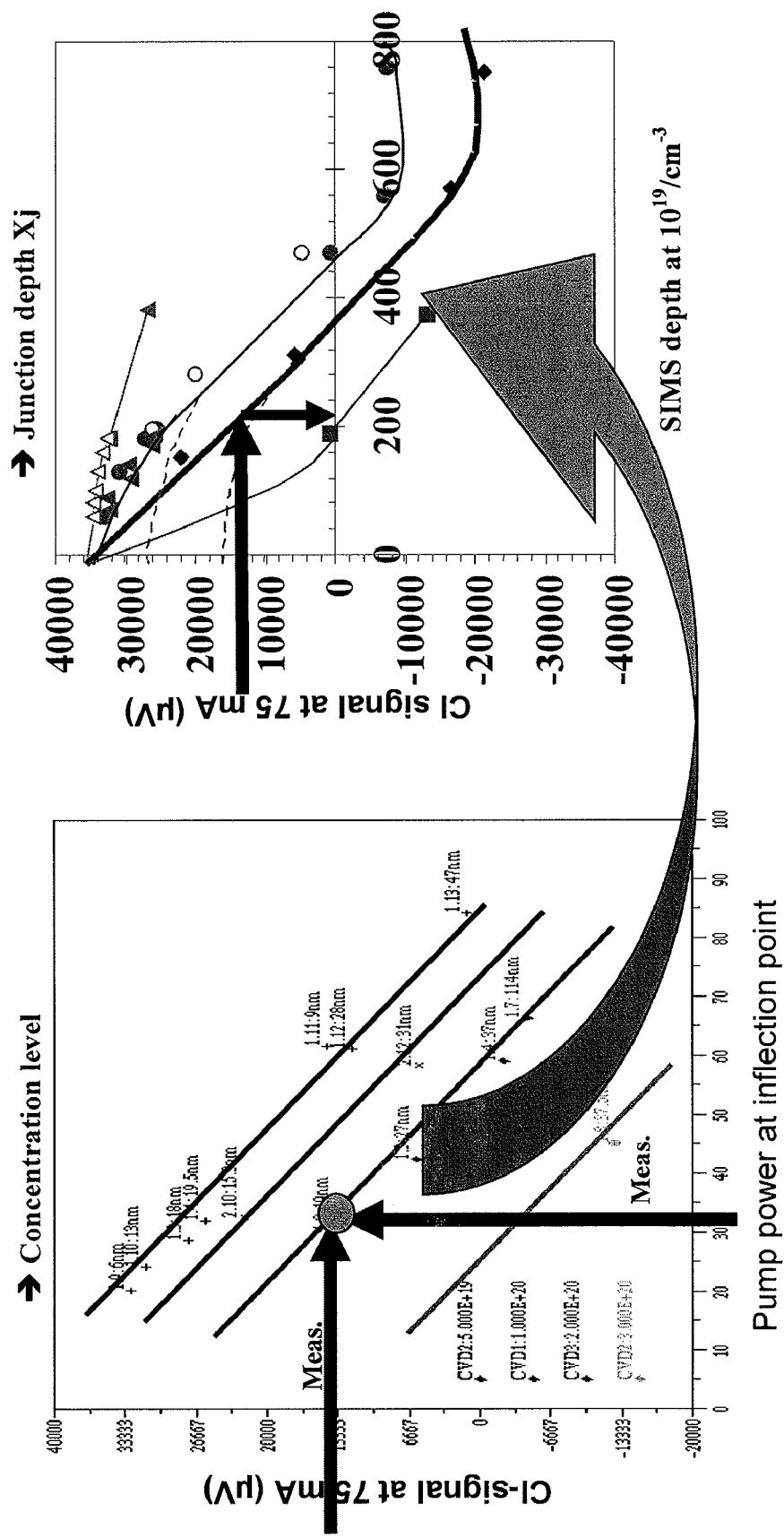
FIG. 13 briefly illustrates an embodiment of the method.

FIG. 10 shows the experimental correlation of the CI-signal, taken at a predetermined reference pump power, for example at 75 mA pump power (as indicated in FIG. 6), versus the pump laser power at the inflection point of the power curve, i.e. the inflection pump laser power, for CVD structures. The experimental data clearly show a systematic, slowly varying, monotonically decreasing correlation between the CI-signal and the inflection pump laser power. Curve 24 in FIG. 10 shows the CI-signal versus the pump laser power at the inflection point for a dopant concentration of $5e19$ $cm^{-3}$, curve 25 for a dopant concentration of $1e20$ $cm^{-3}$, curve 26 for a dopant concentration of $2e20$ $cm^{-3}$ and curve 27 for a dopant concentration of $3e20$ $cm^{-3}$. Furthermore, these correlation curves 24 to 27 lie systematically lower for increasing carrier concentration levels and are parallel to each other. It has to be noted that, when another value is selected for the pump laser power, for example 50 mA, another part of the dopant profile will be screened. It has therefore to be kept in mind that the lower the pump laser power is, the less excess carriers are created and the more the N(z) curve in FIG. 4 will be shifted downwards, hence creating a CI-signal deeper into the substrate. It could be envisaged to create sets of correlation curves as shown in FIG. 13 (see further) for different selected values of the CI-signal. For each set of curves, one point (concentration versus depth) of the actual dopant profile could be determined. If sufficient correlation curves are created, the complete dopant profile may be determined. In FIG. 10, the marker labels indicated at the measuring points refer to the junction depth in nm at which measurements have been carried out.

Figure 11:
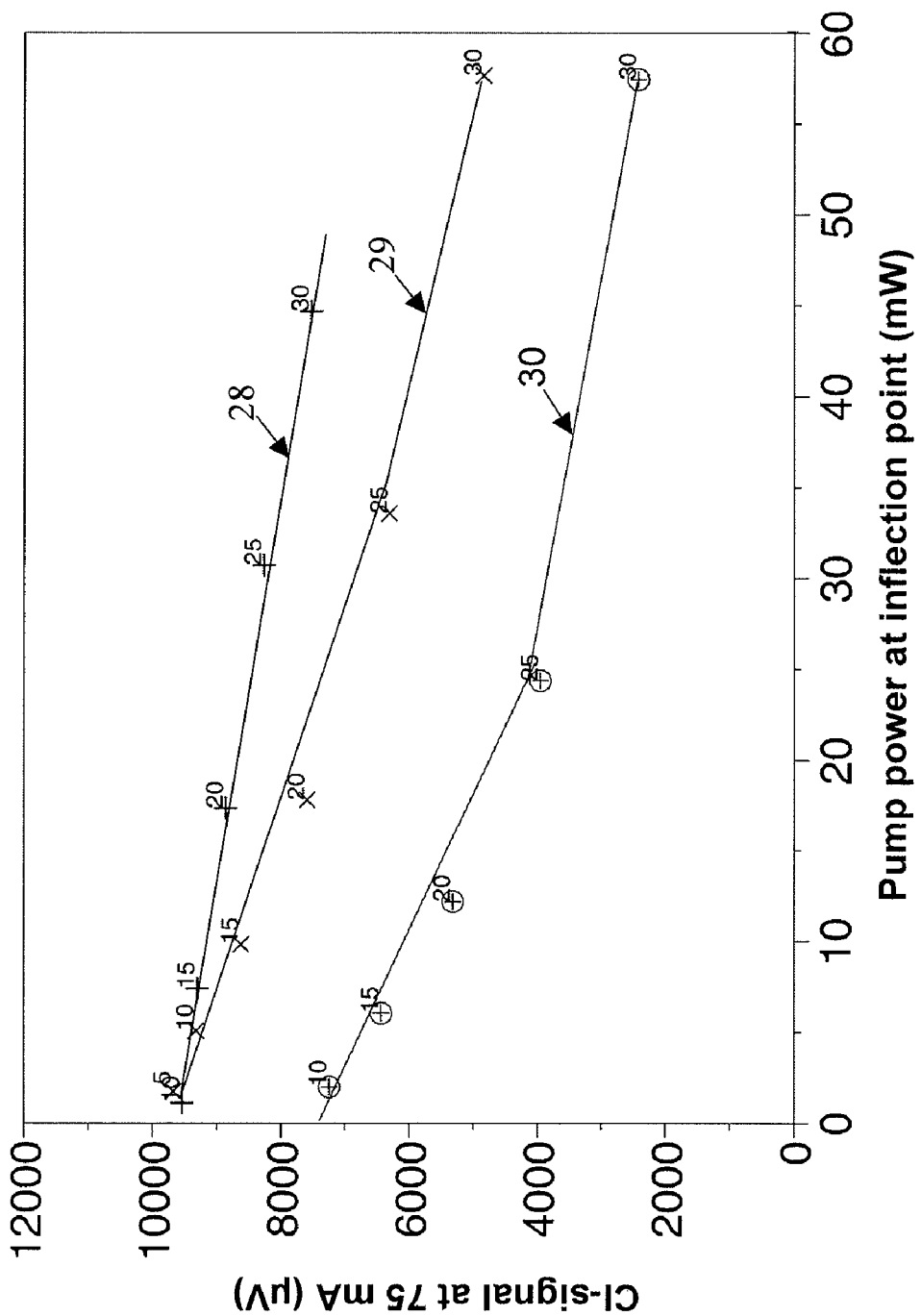
FIG. 11 shows a simulated (Medici) correlation of the CI-signal at a pre-selected pump power of 75 mA versus pump laser power at the power curve inflection point for different CVD samples with different dopant concentrations according to an embodiment of the present invention, illustrating the correspondence between correlation curves obtained by experimentation and simulation for experimental dopant profiles.

FIG. 11 shows the results of a series of device simulations of the CI-signal, taken at the reference pump laser power, for example, 75 mA pump laser power (as indicated in FIG. 6), versus the pump laser power at the inflection point of the power curve, i.e. the inflection pump laser power, for CVD structures. In the example given, the structures may have a box-like dopant profile. It can be seen that the simulated data displays a monotonic behavior. The pump laser power at the inflection point increases with monotonically varying CI-signal, leading to an downward directed curve, as can be seen in FIG. 11, i.e. there is a unique correlation between the abscise and the ordinate, this correlation being dependent on the peak concentration of the doping profile. The curves 28 to 30 illustrated in FIG. 11 are for high peak concentration levels, i.e. peak concentration levels above $1e19$ $cm^{-3}$: Curve 28 shows the results for a CVD layer with peak concentration of $5e19$ $cm^{-3}$, curve 29 for a CVD layer with peak concentration of $7e19$ $cm^{-3}$ and curve 30 for a CVD layer with peak concentration 1e20 cm$^{-3}$. The marker labels shown at each point in the curves 28 to 30 in FIG. 11 are meant to indicate the junction depth in nm at which measurements are performed.

Figure 12A:
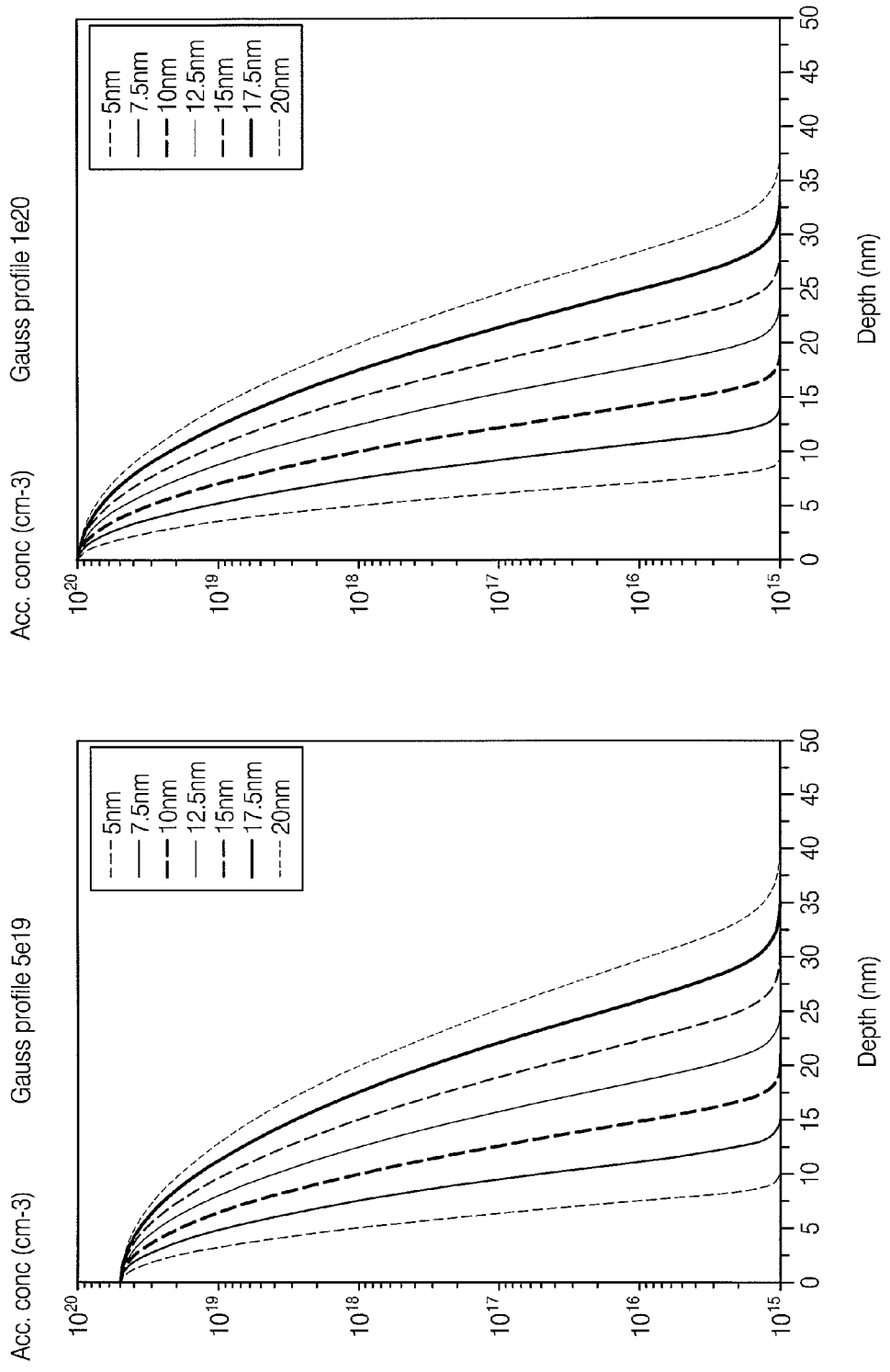
FIG. 12(a) shows dopant profiles obtained by simulation for various ion implantation and annealing conditions according to an embodiment of the invention, FIG. 12 (b) shows a simulated (Medici) correlation of the CI-signal at a predetermined pump power of 75 mA versus pump laser power at the power curve inflection point for the simulated dopant profiles of FIG. 12(a).

In FIG. 12a, dopant profiles are illustrated which are obtained by simulation for various ion implantation and annealing conditions according to embodiments. FIG. 12a illustrates a range of Gaussian profiles which have been used to create FIG. 12b.

Figure 12B:
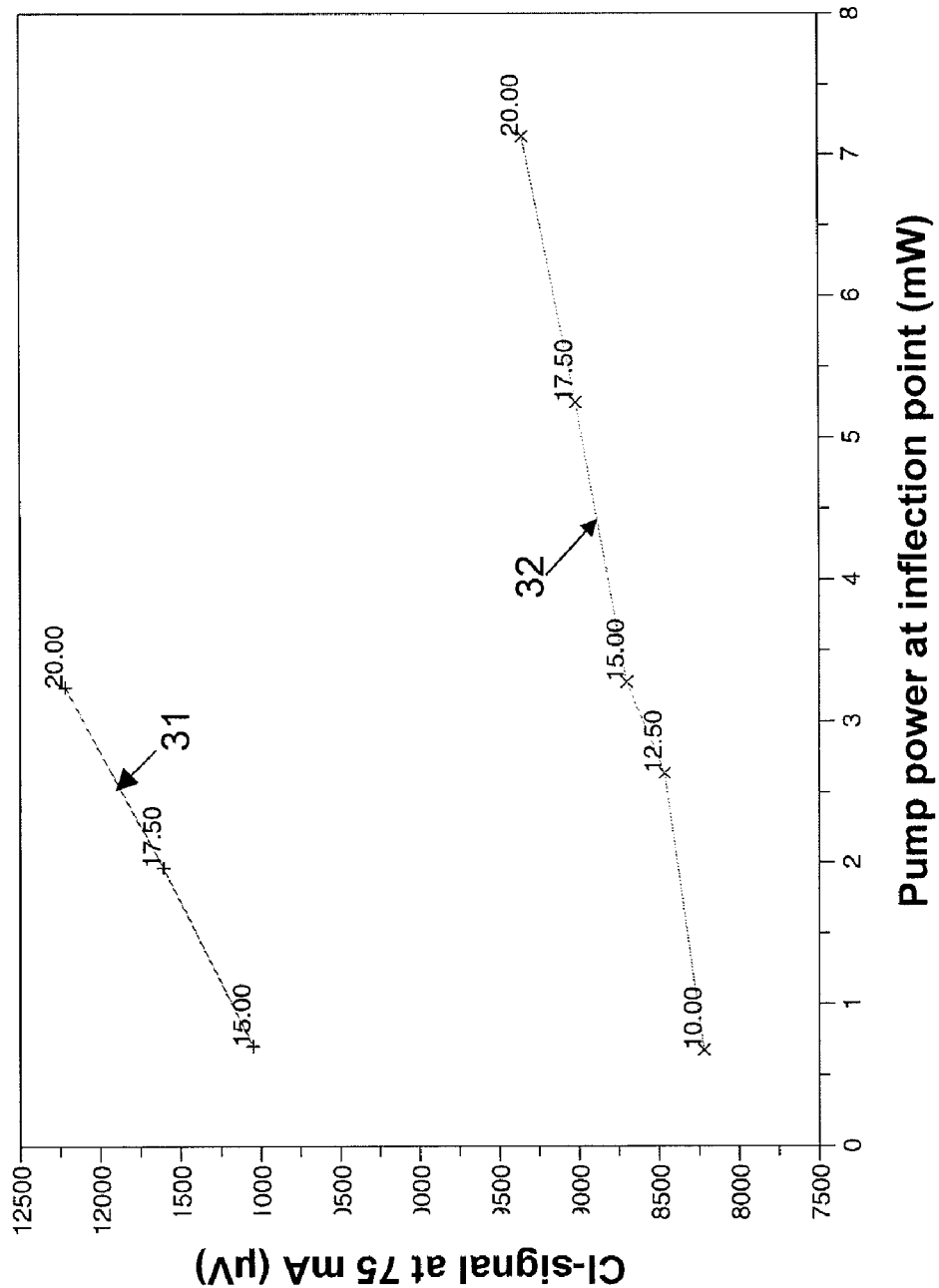

FIG. 12b shows the results of a series of device simulations of the CI-signal, taken at the reference pump laser power, for example at 75 mA pump laser power (as indicated in FIG. 6), versus the pump laser power at the inflection point of the power curve, i.e. the inflection pump laser power, for annealed ion implanted structures. It can be seen that a similar behavior as in FIGS. 10 and 11 is observed, i.e. a monotonic varying curve. In FIG. 12b, curve 31 illustrates a power curve for a dopant concentration of 5e19 cm$^{-3}$ while curve 32 illustrates a power curve for a dopant concentration of 1e20 cm$^{-3}$.

Based on FIGS. 2 and 10, FIG. 11 or FIG. 12b, the following algorithm is proposed to independently determine the carrier concentration level and junction depth for unknown semiconductor substrates, such as for example CVD structures or ion implanted or diffused structures. From the measured power curve (FIG. 6 or left hand side of FIG. 9) it is straightforward to determine the inflection pump laser power value (those pump power values for which the second derivative of pump power equals a pre-selected constant, for example but not limited to, zero). From the CI-signal at the reference pump laser power, e.g. 75 mA pump laser power, and the inflection pump laser power the unique value of the carrier concentration value can be determined from FIG. 10. Once the carrier level is known, FIG. 2 is used to extract the corresponding junction depth with high accuracy. This is illustrated in FIG. 11.

Figure 14:
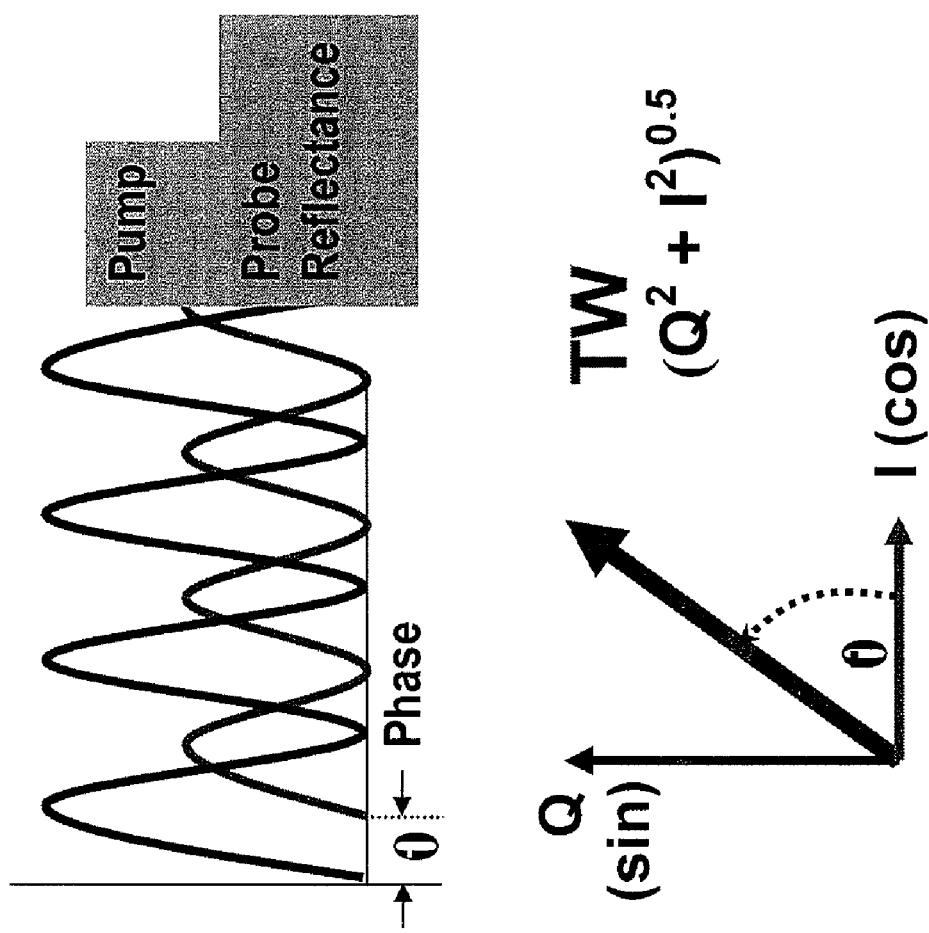
FIG. 14 illustrates the Thermo Probe signal as another example of an optical measurement technique
Figure 15:
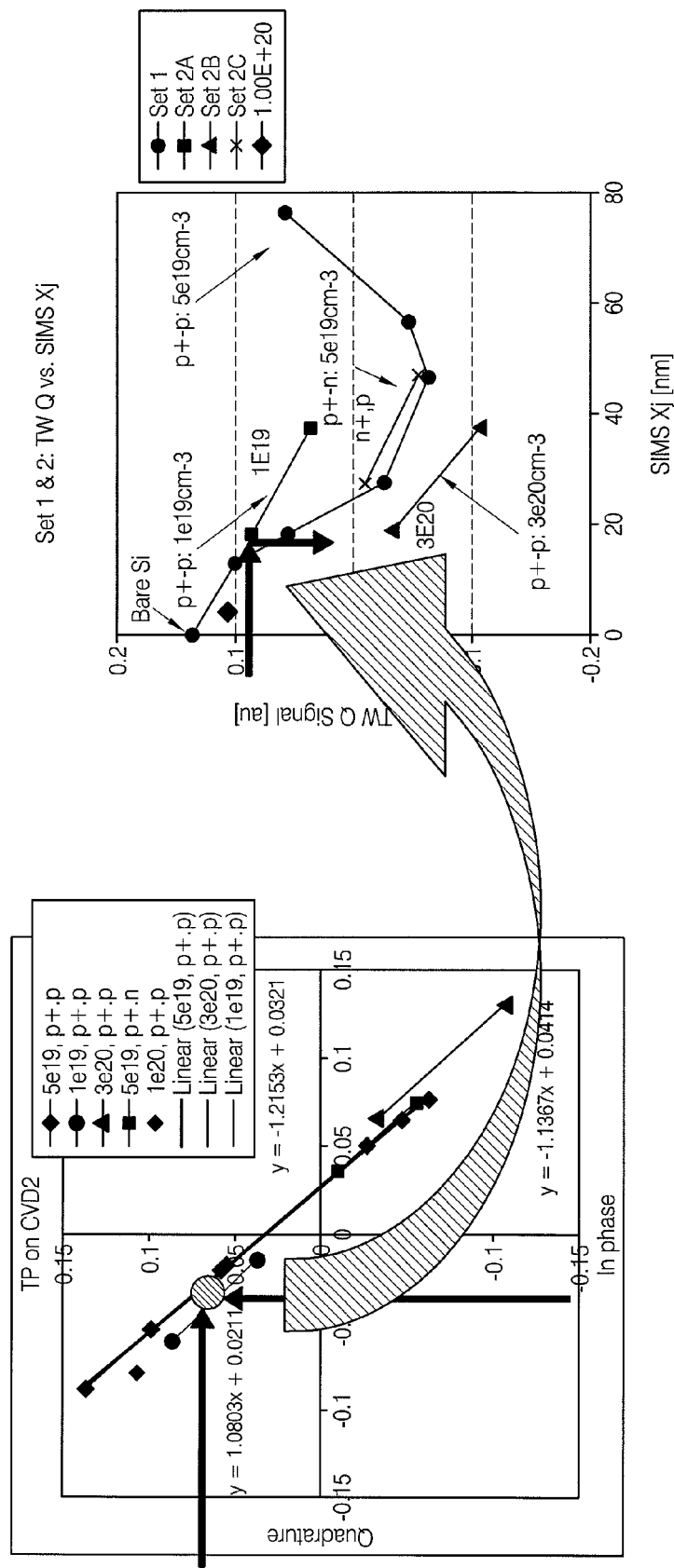
FIG. 15 illustrates the application of one embodiment on the signal obtained by the Thermo Probe measurement technique In the different figures, the same reference signs refer to the same or analogous elements.

Yet another embodiment is illustrated by FIGS. 14 and 15. FIG. 14 illustrates the signal obtained by the Thermo Probe technique also called Thermawave technique or thermal wave technique. This optical measurement technique is discussed in "Nondestructive analysis of ultrashallow junctions using thermal wave technology" by Lena Nicolaides et al. in Review of Scientific Instruments, volume 74, number 1, January 2003. FIG. 14 shows the signal of the pump laser ("pump") and the reflected probe laser ("probe reflectance") signal as function of time. Between both signals there is typically a phase difference $\Theta$ as indicated in FIG. 14. The amplitude TW of the reflected signal is also shown in FIG. 14. This amplitude can be split into two components. One component I is in phase with the pump laser signal (I=TW*cos($\Theta$)) while the other component is in 90° phase difference with the pump laser signal (Q=TW*sin($\Theta$)). FIG. 15 illustrates the application of the embodiment using the Thermo Probe signal TW. This TW signal is again measured at a predetermined power signal for various samples, having different dopant profiles, each dopant profile being characterized by a peak concentration and junction depth. As is shown in FIG. 15 the Q and I component of the TW signal can be correlated in a unique way, the correlation being dependent on the dopant profile in the semiconductor substrate. As shown on the Q-I plot for various peak concentrations (p-type implant, i.e. B, in p-type substrate (p+−p): 1e19 cm$^{-3}$, 5e19 cm$^{-3}$, 1e20 cm$^{-3}$, 3e20 cm$^{-3}$; p-type implant, i.e. B, in n-type substrate (p+−n): 5e19 cm$^{-3}$) this relationship is again monotonically varying. Hence from a given TW signal measured at a predetermined power signal level, the Q (Quadrature component) and I (in-phase component) components can be derived and plotted on the correlation graph of FIG. 15 (left). From this pair of Q-I data the unique carrier concentration value can be determined as shown by the arrows in FIG. 15 (left). This unique value is then used together with the Q component of this TW signal to determine the corresponding junction depth as shown by the arrows in FIG. 15 (right). FIG. 15 (right) is similar to FIG. 2 or FIG. 13 (right): it shows the measured signal at a predetermined pump power level as function of the junction depth for various dopant profiles characterized by their peak concentration level.

The method of the foregoing embodiments allows, in a non-destructive way, to determine the peak dopant concentration and junction depth in a particular semiconductor substrate, independent from each other, from a same measurement.

It is to be understood that although preferred embodiments, specific constructions and configurations, as well as materials, have been discussed herein for devices according to the present invention, various changes or modifications in form and detail may be made without departing from the scope and spirit of this invention. For example, the substrate used in the description above is silicon, but may as well be any other suitable semiconductor material such as e.g. germanium (Ge), silicon-germanium (SiGe) or galliumarsenide (GaAs).

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. An optical measurement method of determining a dopant concentration profile, characterized by a concentration level and a junction depth, of a semiconductor substrate of a semiconductor material, the method comprising:

measuring first amplitudes of measured reflection signals obtained by creating different concentrations of excess carriers and impinging a probe laser beam at least partially reflected by the excess carriers on the semiconductor substrate having a dopant profile characterized by a concentration level and a junction depth;

determining first correlations between the first amplitudes and the dopant concentration level for a dopant in the substrate;

measuring a second amplitude of a reflection signal obtained by creating excess carriers and impinging a probe laser beam at least partially reflected by the excess carriers, on the semiconductor substrate having a dopant profile, characterized by a concentration level and a junction depth;

determining second correlations between the first amplitudes and the junction depth of the dopant profile of the semiconductor substrate; and determining from the first and second correlations and the second amplitude the junction depth and the dopant concentration level for the semiconductor substrate.

2. An optical measurement method according to claim 1, wherein creating excess carriers comprises impinging a pump laser beam.

3. An optical measurement method according to claim 1, wherein measuring the first or the second amplitude comprises:
measuring the reflection signal as a function of the pump power level, thus yielding a power curve, the power curve showing an inflection point,
determining a first pump power level value corresponding to the inflection point, and
determining the reflection signal at a second pump power level.

4. An optical measurement method according to claim 3, wherein determining a junction depth and a carrier concentration level for the semiconductor substrate comprises determining a carrier concentration level from the reflection signal at the second pump power level and the first pump power level corresponding to the inflection point.

5. An optical measurement method according to claim 3, wherein
determining the reflection signal is carried out at a first predetermined value of the pump laser power;
and wherein determining the carrier concentration level from the reflected signal is carried out at a second predetermined value of the pump laser power, the first pump laser power corresponding to the inflection point.

6. An optical measurement method according to claim 3, wherein the semiconductor substrate comprises a highly-lowly doped structure.

7. An optical measurement method according to claim 6, wherein the semiconductor substrate has a box-like dopant profile.

8. An optical measurement method according to claim 3, further comprising determining a junction depth of the semiconductor substrate from the reflection signal at a second pump laser power and the determined carrier concentration level.

9. An optical measurement method according to claim 3, wherein generating a reflection signal comprises:
generating an excess charge carrier profile in the semiconductor substrate by focusing a pump laser beam onto the semiconductor substrate, and
illuminating the semiconductor substrate with a probe laser beam.

10. An optical measurement method according to claim 3, wherein the inflection point is determined based on a constant value of the second derivative of the power curve.

11. An optical measurement method according to claim 10, wherein the constant value of the second derivative of the power curve is close to zero.

12. An optical measurement method according to claim 3, wherein the optical measurement method is based on carrier illumination.

13. An optical measurement method according to claim 12, wherein the pump laser beam has a fixed wavelength of approximately 830 nm.

14. An optical measurement method according to claim 1, wherein measuring the first or the second amplitude of the reflection signal comprises:
determining a component of the reflection signal which is in phase with the pump laser signal; and
determining a component of the reflection signal which is in 90° phase difference with the pump laser signal.

15. An optical measurement method according to claim 14, wherein the pump laser signal is at a pre-determined power level.

16. An optical measurement method according to claim 14, wherein determining a junction depth and a carrier concentration level for the semiconductor substrate comprises determining a carrier concentration level from an amplitude of the reflection signal which is in phase with the pump laser signal and from an amplitude of the reflection signal which is in 90° phase difference with the pump laser signal.

17. An optical measurement method according to claim 16, wherein determining a junction depth and a carrier concentration level for the semiconductor substrate comprises determining a junction depth from the determined component of the reflection signal which is in 90° phase difference with the pump laser signal and from the determined carrier concentration level.

18. An optical measurement method according to claim 14, wherein the semiconductor substrate is a highly-lowly doped structure.

19. An optical measurement method according to claim 18, wherein the semiconductor substrate has a box-like dopant profile.

20. An optical measurement method according to claim 14, wherein generating a reflection signal comprises:
generating an excess charge carrier profile in the semiconductor substrate by focusing a pump laser beam onto the semiconductor substrate, and
illuminating the semiconductor substrate with a probe laser beam.

21. An optical measurement method according to claim 14, wherein the optical measurement method is based on thermal wave technology.

22. An optical measurement method according to claim 21, wherein the pump laser beam has a fixed wavelength of approximately 790 nm.

23. An optical measurement method of calibrating a substrate of a semiconductor material having a dopant profile, characterized by a concentration level and a junction depth, in the substrate, the method comprising:
determining a first set of correlation curves between
first amplitudes of measured reflection signals obtained by creating different concentrations of excess carriers in the substrate and impinging a probe laser beam at least partially reflected by the excess carriers, on the substrate and
dopant concentration levels for a dopant in the substrate; and
determining a second set of correlation curves between the amplitudes of the measured reflected signal and junction depths of the substrate,
wherein the process of determining a first set of correlation curves comprises:
providing at least two semiconductor substrates with predetermined different dopant profiles, each dopant profile characterized by a concentration level and junction depth,
measuring for each of the at least two semiconductor substrates a first amplitude of reflected signals, the reflecting signals being generated by
creating different concentrations of excess carriers in the sample, and
a probe laser beam at least partially being reflected by the excess carriers, on each of the at least two semiconductor substrates, and determining a first correlation between the first measured amplitude of each reflected signal and the concentration level of the at least two semiconductor substrates.

24. An optical measurement method according to claim 23, wherein determining a second set of correlation curves comprises determining a second correlation between the first measured amplitude of each reflected signal and the junction depth of the at least two semiconductor substrates.

* * * * *